United States Patent [19]

Kohayakawa et al.

[11] 4,146,310
[45] Mar. 27, 1979

[54] OPHTHALMOSCOPIC OPTICAL SYSTEM

[75] Inventors: Yoshimi Kohayakawa; Isao Matsumura, both of Yokohama, Japan

[73] Assignee: Canon Kabushiki Kaisha, Tokyo, Japan

[21] Appl. No.: 771,738

[22] Filed: Feb. 24, 1977

[30] Foreign Application Priority Data

Mar. 9, 1976 [JP] Japan .................................. 51/25413

[51] Int. Cl.² .............................................. A61B 3/14
[52] U.S. Cl. ..................................................... 351/7
[58] Field of Search ........................ 351/7, 16; 354/62

[56] References Cited

U.S. PATENT DOCUMENTS

| 3,533,683 | 10/1970 | Stark et al. | 351/6 X |
| 3,851,954 | 12/1974 | Kato et al. | 351/7 |
| 3,936,844 | 3/1974 | Matsumura | 354/62 |

Primary Examiner—Paul A. Sacher
Assistant Examiner—Rodney B. Bovernick
Attorney, Agent, or Firm—Toren, McGeady and Stanger

[57] ABSTRACT

An ophthalmoscopic photographing and observing system eliminates rays of light reflected and scattered at the cornea and the crystalline lens of a human eye. An illuminating optical system is provided with light shielding stops at positions conjugate to the corneal surface, the iris, and the rear face of the crystalline lens of an eye being examined. The sizes of these light shielding stops are such that an image of the stop conjugate to the corneal surface covers an area on the cornea where the light reflected by the fundus of the eye passes through the cornea covered with an image of the stop which is conjugate to the corneal surface; an image of the stop which is conjugate to the rear surface of the crystalline lens covers an area on the rear face of the crystalline lens where the light reflected by the fundus of the eye passes through. A ring-shaped aperture stop is conjugate to the iris.

8 Claims, 6 Drawing Figures

OPHTHALMOSCOPIC OPTICAL SYSTEM

BACKGROUND OF THE INVENTION

This invention relates to an ophthalmoscopic photographing and observing system with an eye fundus illuminating optical system and more particularly to a system which eliminates scattering rays of light produced inside and at the rear face of the crystalline lens of an eye which is being examined.

Illumination rays of light that are reflected by a corneal surface cause a flare in a photographic image when they mix with a photographing light. To prevent such inconvenience, a ring-shaped aperture stop has been previously provided within an illuminating optical system of an eye fundus (or retinal) camera at a position conjugate to the corneal surface, as described in a British Pat. No. 799,812.

In accordance with such a method of removing the reflected light, a ring-shaped illuminating light beam is projected upon the eye through the peripheral area of the pupil of the eye (that is, an aperture of the iris). The photographic beam of light reflected by the fundus of the eye is allowed to pass through the middle part of the pupil. An area on the cornea through which one of the two light passes is thus arranged to overlap another area of the cornea through which the other light flux passes, so that the undesired light reflected by the cornea is removed.

A U.S. Pat. No. 3,851,954 discloses another type of arrangement, wherein the reflection of the eye fundus illuminating light is prevented at the front and also at the rear of the crystalline lens of an eye being examined. A center obscuring stop is positioned either conjugate to the front face of the crystalline lens or conjugate to an intermediate point between the front face and the rear face of the crystalline lens.

The present inventors have discovered an ophthalmoscopic camera that permits photographing without the use of mydriatics.

The ophthalmoscopic camera which does not require the use of mydriatics differs from the conventional ophthalmoscopic camera in that the diameter of the above stated ring-shaped aperture is smaller for the former than for the latter. The reason for this is that the diameter of a pupil is smaller when no mydriatics are used than when a mydriatics is used. When they attempted to use the above-mentioned new camera, the present inventors found a flare remaining in the image obtained. It was also discovered that an illuminating light beam directed toward the fundus of an eye was scattered by the film of crystalline lens of the eye and by the inner liquid thereof such that scattering of the light caused the flare in the image. Since the liquid inside a crystalline lens usually becomes muddier with advance of age, such scattered light increases in aged people.

It is also conceivable that such a flare in an image is caused by the increased intensity of a flash light due to a smaller diameter of the ring-shaped aperture and by a crystalline lens passing optical path which is closer to the optical axis due to the smaller diameter of the ring-shaped aperture.

In the accompanying drawings, FIG. 5 illustrates an eye being examined. Here, reference symbol P indicates a cornea; Q indicates a crystalline lens; Q1 indicates the front face of the crystalline lens and Q2 indicates the rear face thereof. A reference symbol C indicates an image of a ring-shaped aperture, a part indicated by hatching representing its shaded area. An illuminating light passes through the areas between the pairs of lines L and l, while a photographing light passes between lines l. In order to prevent the illuminating light from being reflected at the part R on the front face Q1 of the crystalline lens, an image D of a center obscuring stop is formed on the front face Q1. The light reflected by the rear face Q2 is thus removed by the shadow of the image D.

To prevent the illuminating light from being scattered through the crystalline lens, the image D of the obscuring stop must cover at least a scattering face S on the rear face Q2. For this purpose, if the image of the obscuring stop is made larger, the quantity of illuminating light would decrease substantially. To avoid such decrease in illuminating light, the size of the ring-shaped aperture must be increased accordingly and such arrangement causes inconvenience.

SUMMARY OF THE INVENTION

It is a first object of this invention to provide a system wherein illuminating light is prevented from being scattered inside a crystalline lens and also at the rear face thereof. If the rear face of the crystalline lens is sufficiently covered by an image of a stop, the light scattering part inside the crystalline lens can be kept within the shadow of the image of the stop.

A second object of this invention is to provide a system in which a ring-shaped aperture stop has a minimal diameter. It is important for an ophthalmoscopic camera that uses no mydriatics to avoid the use of a ring-shaped aperture stop of an increased diameter. The camera system is provided with an observing system composed of a photodetecting tube and a monitoring means.

In accordance with this invention, a ring-shaped aperture stop or the like is provided within an illuminating optical system of an ophthalmoscopic optical system at a position virtually conjugate to the iris of the eye being examined. A first light shielding stop is also in the illuminating optical system at a position virtually conjugate to the rear face of the crystalline lens of the eye while a second light shielding stop is disposed in the illuminating optical system at a position virtually conjugate to the corneal surface of the eye.

The size of the image of the first light shielding stop is arranged to be able to cover the area where the effective photographic light passes through the rear face of the crystalline lens. The size of the image of the second light shielding stop is arranged to be able to cover the area where the effective photographic light passes through the corneal surface.

The above and other objects and features of the invention will become apparent from the following description in conjunction with the accompanying drawings.

DESCRIPTION OF PREFERRED EMBODIMENT

In accordance with this invention, an image of a ring-shaped aperture is positioned to be closer to a middle point between the corneal surface and the rear face of the crystalline lens of an eye being examined. Thus the area where the photographic light passes through the rear face of the crystalline lens is reduced.

Figure 1:
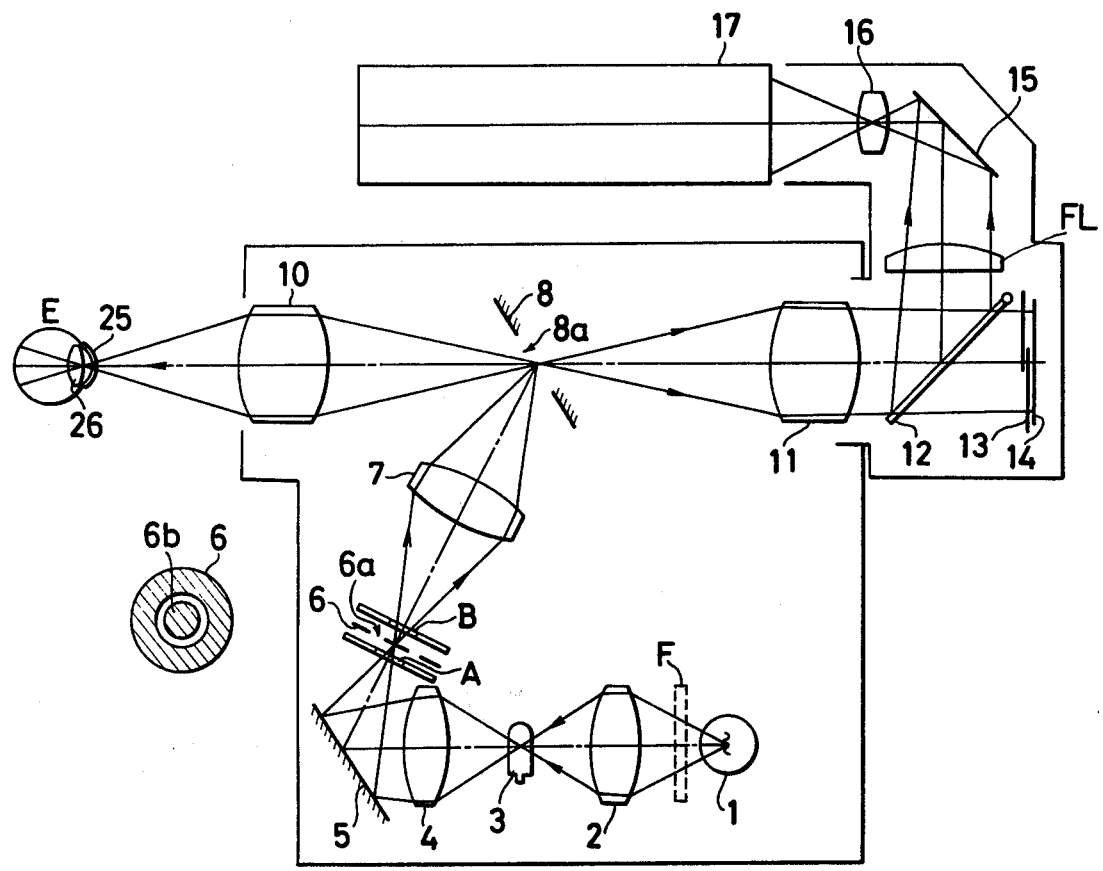
FIG. 1 is a sectional view illustrating an embodiment of this invention.

FIG. 1 is a side sectional view illustrating an eye fundus camera which does not require mydriasis. In FIG. 1, reference numeral 1 indicates an infrared ray light source, composed of a combination of an infrared or near infrared filter F and a tungsten filament lamp. Reference numeral 2 indicates a condenser lens, which first forms an image of the infrared ray light source 1 on a tube 3. Reference numeral 4 indicates another condenser lens, 5 indicates a mirror, and, 6 indicates a light shielding plate which is provided with an annular aperture 6a. The condenser lens 4 forms an image of the strobe tube 3 and the image of the light source 1 on the light shielding plate 6. Reference numeral 7 indicates a relay lens and 8 indicates a perforated oblique mirror. The relay lens 7 forms an image of the aperture 6a on the perforated oblique mirror. The above stated elements 2 through 8 constitute an illuminating optical path.

Reference numeral 10 indicates an objective; 11 indicates an image forming lens; 12 indicates a mirror which retreats during the photographic operation; 13 indicates a shutter; 14 indicates a film; 15 indicates a mirror; 16 indicates an image forming lens; and 17 indicates an infrared image tube. The film 14 is adjustable to be conjugate to the fundus of an eye in relation to the objective 10 and the image forming lens 11. The light receiving face of the image tube 17 is adjustable to be conjugate to the eye fundus in relation to the objective 10, the image forming lens 11 and the image forming lens 16. The infrared image tube 17 receives a reflection light from the eye fundus to convert image data into an electrical signal. In the illustration, an image display monitor is omitted. The objective 10, an aperture 8a and the image forming lens 11 constitute a photographic system, while the mirror 12, a field lens FL, the mirror 15 and the image forming lens 16 constitute a view finding system.

As described above, an image of the annular aperture 6a is formed on the perforated oblique mirror 8. The image of the annular aperture is again formed on the pupil of the eye E through the objective 10. Thus, at the pupil, the arrangement forms a light converging area corresponding to the aperture 6a and an unilluminated area corresponding to the middle part 6b of the light shielding plate 6. The eye fundus is thus illuminated by the light from the light converging area.

Figure 2:
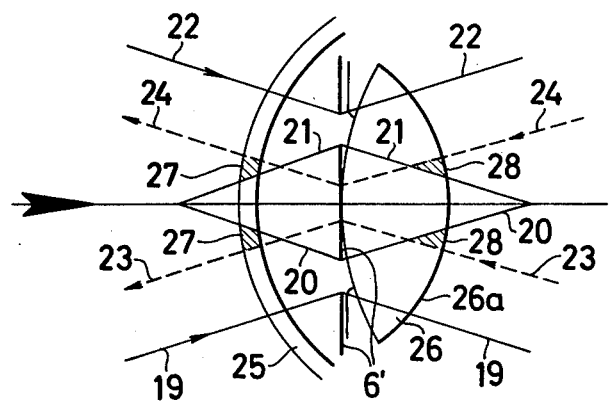
FIG. 2 is a sectional view illustrating an eye being examined with an image of a ring-shaped aperture stop formed thereon.

FIG. 2 illustrates the front portion of an eye being examined with the annular aperture used for illuminating it. In FIG. 2, reference numeral 25 indicates a cornea; 26 indicates a crystalline lens; 26a indicates the rear face of the crystalline lens; and 6' indicates an image of the light shielding plate. Light flux passes through an area between solid lines 19 and 20 and also between solid lines 21 and 22 while the illumination light does not reach a lozenge-shaped area (shadow) between solid lines 20 and 21. When a photographing light flux reflected by the eye fundus passes through an area between broken lines 23 and 24, the hatched areas 27 and 28 of the cornea 25 and the crystalline lens 26 are jointly shared by the photographic light and the illuminating optical path. A part of the illuminating light reflected and scattered at these parts, therefore, mixes with the returning photographic light. If the angle of view of the objective is narrow, the slant of the solid lines 20 and 21 to the image 6' is gentle and, accordingly the hatched areas 27 and 28 are small, so that such undesirable light is reduced to a minimum. Further, if the annular aperture has a large diameter, i.e. if the diameter of the middle light shielding part 6b is great, the lozenge-shaped light shielding area will be sufficiently large to hinder such undesired light.

However, where it is difficult to make the diameter of the ring-shaped (or annular) aperture greater as described in the second object of this invention, the scattered light in hatched areas 27 and 28 must be eliminated. For this purpose, small light shielding pieces A and B are disposed before and after the ring-shaped aperture plate 6. Such a light shielding piece A or B is made by providing a black-colored small circle on a transparent flat plate.

Figure 3:
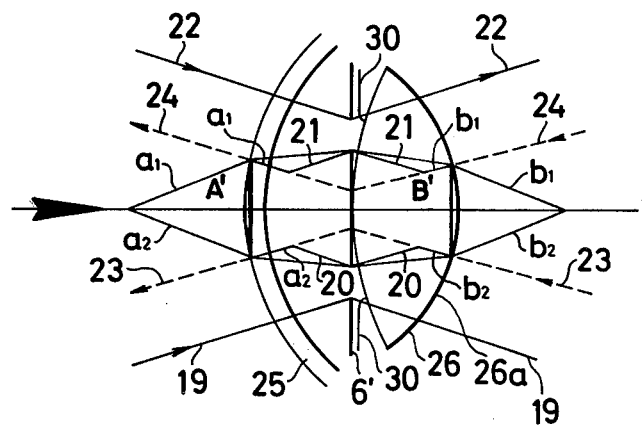
FIG. 3 is a sectional view illustrating the eye on which an image of a ring-shaped aperture stop and images of light shielding stops are formed.
Figure 5:
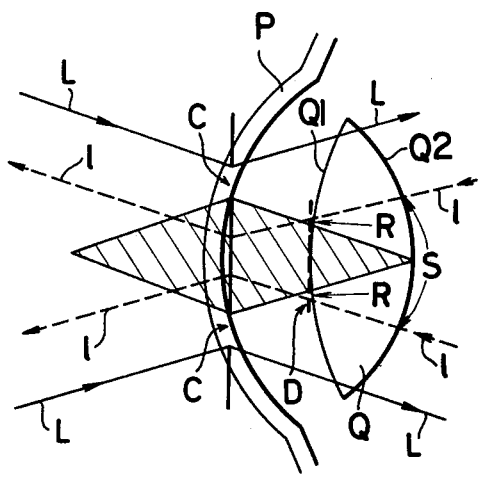
FIG. 5 is a cross section of an eye being examined.
Figure 4:
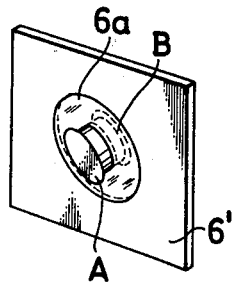
FIG. 4 is an oblique view illustrating a three dimensional stop.

The circular stop A is disposed at a position conjugate to the vicinity of the apex cornea of the in relation to the relay lens 8 and the objective 10, with the image 6' of the light shielding plate 6 (annular aperture 6a) adjusted to coincide approximately with the position of the pupil of the eye (aperture of iris 30). The center of the circular stop A is arranged to coincide with the optical axis at this position. The diameter of the circular stop A is determined in relation to the magnification of the relay lens and the objective 10 and also in relation to the diameter of the area on the cornea through which the light reflected by the eye fundus (photographing light) passes. Circular stop B is also disposed at a position conjugate to the vicinity of the apex of the rear face 26a of crystalline lens 26 in relation to the relay lens 7, mirror 8 and the objective 10. The stop is arranged to have a large enough diameter to enable its image to cover the area on the rear face of the crystalline lens through which the light reflected by the eye fundus passes. FIG. 3 illustrates the operation of the same embodiment example as FIG. 1 as applied to an eye, including light shielding stops A and B. In FIG. 3, reference symbol A' indicates an image of the light shielding stop A; B' indicates an image of the light shielding stop B; and an area between solid lines a1 and a2 represents a light shielded area brought about by the image A' while another area between solid lines b1 and b2 represents a light shielded area brought about by the image B'. The same parts as those shown in FIG. 2 are indicated by like reference numerals.

As apparent from the illustration, the area through which the light reflected by the eye fundus passes (between broken lines 23 and 24) is within the area shielded from the eye fundus illuminating light. This arrangement, therefore, effectively prevents the undesirable light which is produced by the reflection or scattering of the illuminating light by the cornea and the crystalline lens from mixing with the photographic light reflected by the eye fundus. Further, the above stated arrangement may be replaced by a three dimensional light shielding unit, prepared by consolidating the middle light shielding part 6b of the light shielding plate 6 and the stops A and B into one unit as illustrated in FIG.

Figure 6:
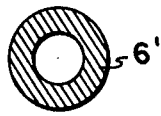
FIG. 6 is a plan view of a stop having a circular opening without a center masked portion that forms a ring.

4. Also, the middle light shielding part 6b may be omitted. See FIG. 6.

With an eye fundus camera (or a retinal camera) as described in this invention, the strobe tube 3 emits light to illuminate the eye fundus; the eye fundus reflection light forms an image on the film 14 through the objective 10 and the image forming lens 11, and a photograph of good contrast is obtained because there is included no undesirable light.

What is claimed is:

1. An ophthalmoscopic optical system including:
   objective means which confronts an eye being examined; an image forming lens group which is arranged on the image side of said objective means;
   an illuminating system for illuminating the fundus of the eye, the illuminating system comprising at least one light source, a condenser lens and relay lens means;
   reflecting means which is disposed between said objective means and said image forming lens group and which serves to reflect the light emitted from said illuminating system toward said objective means;
   a mask stop having a circular aperture provided in said illuminating system and substantially conjugate to an iris of the eye;
   a first stop provided in said illuminating system at a position which is substantially conjugate with a rear surface of a crystalline lens of the eye, said first stop being large enough so its image covers an area on the rear surface of the crystalline lens through which photographic light reflected by the fundus of the eye passes; and
   a second stop provided in said illuminating system at a position which is substantially conjugate to a cornea of the eye, said second stop being arranged to be large enough so its image covers the area on the cornea through which photographic light reflected by the fundus of the eye passes.

2. An ophthalmoscopic optical system according to claim 1 wherein a movable mirror is positioned on the image side of said image forming lens group; and an effective photographing light flux directed by said image forming lens groups and reflected by said movable mirror is formed into an image on a photodetecting surface of a photodetecting means through a light transmitting system.

3. An ophthalmoscopic optical system according to claim 2 wherein said photodetecting means is sensitive to infrared rays.

4. An ophthalmoscopic optical system according to claim 1 wherein said first and second stops are arranged adjacent to said mask stop.

5. An ophthalmoscopic optical system according to claim 4, wherein said stop having the circular aperture includes a center obscuring zone that forms a ring-shaped opening.

6. An ophthalmoscopic optical system according to claim 1, wherein said stop having the circular aperture includes a center obscuring zone that forms a ring-shaped opening.

7. An ophthalmoscopic optical system according to claim 2, wherein said stop having the circular aperture includes a center obscuring zone that forms a ring-shaped opening.

8. An ophthalmoscopic optical system according to claim 3, whrein said stop having the circular aperture includes a center obscuring zone that forms a ring-shaped opening.

* * * * *